(12) United States Patent
Favaloro et al.

(10) Patent No.: US 9,395,284 B2
(45) Date of Patent: Jul. 19, 2016

(54) AUTOMATED SYSTEM AND METHOD OF TREATING TISSUE SAMPLES ON SLIDES

(71) Applicant: LEICA BIOSYSTEMS MELBOURNE PTY LTD, Mount Waverly, Victoria (AU)

(72) Inventors: Anthony Favaloro, Richmond (AU); Luke Restorick, Caulfield South (AU); Michael Houston Drummond, Glen Waverley (AU); Stephen John Bagnato, Mt Waverley (AU)

(73) Assignee: LEICA BIOSYSTEMS MELBOURNE PTY LTD, Victoria (AU)

( * ) Notice: Subject to any disclaimer, the term of this patent is extended or adjusted under 35 U.S.C. 154(b) by 0 days.

(21) Appl. No.: 14/358,480

(22) PCT Filed: Nov. 15, 2012

(86) PCT No.: PCT/AU2012/001413
§ 371 (c)(1),
(2) Date: May 15, 2014

(87) PCT Pub. No.: WO2013/071357
PCT Pub. Date: May 23, 2013

(65) Prior Publication Data
US 2014/0329270 A1     Nov. 6, 2014

Related U.S. Application Data

(60) Provisional application No. 61/560,559, filed on Nov. 16, 2011.

(51) Int. Cl.
*G01N 21/00* (2006.01)
*G01N 1/31* (2006.01)
*G01N 35/00* (2006.01)

(52) U.S. Cl.
CPC ............ *G01N 1/312* (2013.01); *G01N 35/0099* (2013.01)

(58) Field of Classification Search
CPC ...................................................... G01N 21/00
See application file for complete search history.

(56) References Cited

U.S. PATENT DOCUMENTS

| 4,155,978 A | 5/1979 | Naono et al. |
| 7,584,019 B2 * | 9/2009 | Feingold et al. ............. 700/245 |

(Continued)

FOREIGN PATENT DOCUMENTS

| CN | 1788201 A | 6/2006 |
| CN | 101021455 A | 8/2007 |

(Continued)

OTHER PUBLICATIONS

Communication dated Jun. 1, 2015, issued by the European Patent Office in corresponding European Application No. 12850388.5.

(Continued)

*Primary Examiner* — Jyoti Nagpaul
(74) *Attorney, Agent, or Firm* — Sughrue Mion, PLLC

(57) ABSTRACT

An automated method and system for treating one or more tissue samples disposed on slides, the system comprising: a controller, a plurality of slide treatment modules arranged to receive ones of the slides; at least one fluid dispensing robot configured by the controller to dispense a plurality of reagents to said ones of the slides received in the slide treatment modules via an output nozzle disposed on the at least one fluid dispensing robot to treat said one or more tissue samples respectively; and at least one pumping means for pumping said reagents to the output nozzle of the at least one fluid dispensing robot from a plurality of reagent containers comprising said reagents, wherein the at least one fluid dispensing robot is configured by the controller to dispense said reagents in a predetermined sequence for each of the slide treatment modules to treat the one or more tissue samples disposed on each of the slides independently.

17 Claims, 11 Drawing Sheets

(56) References Cited

U.S. PATENT DOCUMENTS

| | | |
|---|---|---|
| 2004/0033163 A1 | 2/2004 | Tseung et al. |
| 2009/0232704 A1 | 9/2009 | Dohmae et al. |
| 2009/0325309 A1 | 12/2009 | Favuzzi et al. |
| 2010/0017030 A1 | 1/2010 | Feingold et al. |
| 2010/0178668 A1 | 7/2010 | Elliot et al. |
| 2010/0209298 A1 | 8/2010 | Kalra et al. |
| 2011/0136135 A1 | 6/2011 | Larsen et al. |
| 2011/0174088 A1 | 7/2011 | Watkins et al. |
| 2012/0003121 A1 | 1/2012 | Shibata et al. |

FOREIGN PATENT DOCUMENTS

| | | |
|---|---|---|
| CN | 102159932 A | 8/2011 |
| JP | 53-133484 A | 11/1978 |
| JP | 56-47764 A | 4/1981 |
| JP | 5-281240 A | 10/1993 |
| JP | 6-249762 A | 9/1994 |
| JP | 6-323965 A | 11/1994 |
| JP | 2000-516526 A | 12/2000 |
| JP | 2001-133371 A | 5/2001 |
| JP | 2003-28769 A | 1/2003 |
| JP | 2005-530165 A | 10/2005 |
| JP | 2007-526479 A | 9/2007 |
| JP | 2010-175420 A | 8/2010 |
| JP | 2011-524527 A | 9/2011 |
| WO | 98/04358 A1 | 2/1998 |
| WO | 2004/059441 A2 | 7/2004 |
| WO | 2005/084263 A2 | 9/2005 |
| WO | 2009/152569 A1 | 12/2009 |
| WO | 2010/107042 A1 | 9/2010 |
| WO | 2011/069507 A1 | 6/2011 |

OTHER PUBLICATIONS

Communication dated May 6, 2015, issued by the State Intellectual Property Office of the P.R.C. in corresponding Chinese Application No. 201280067150.3.

Communication dated Mar. 22, 2016 from the Japanese Patent Office in counterpart application No. 2014-541483.

\* cited by examiner

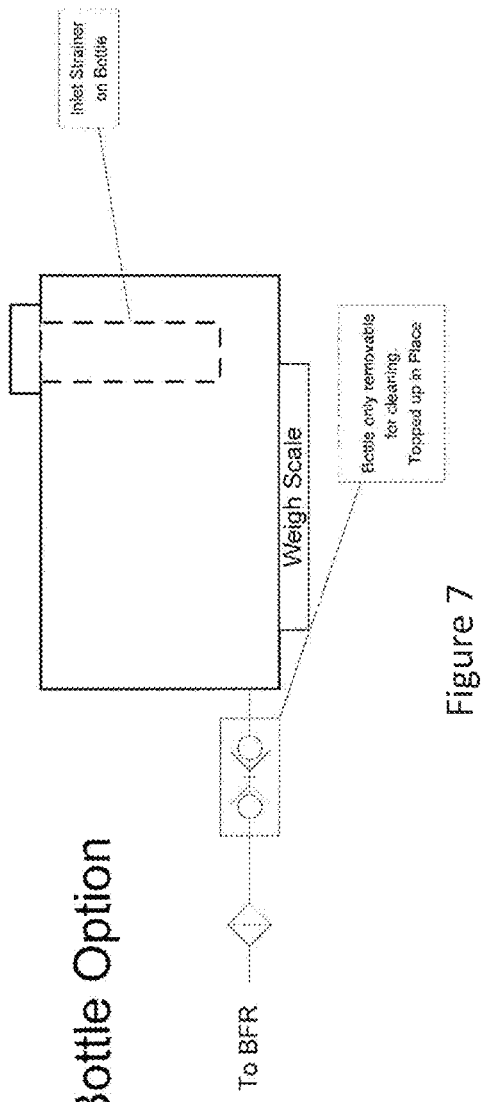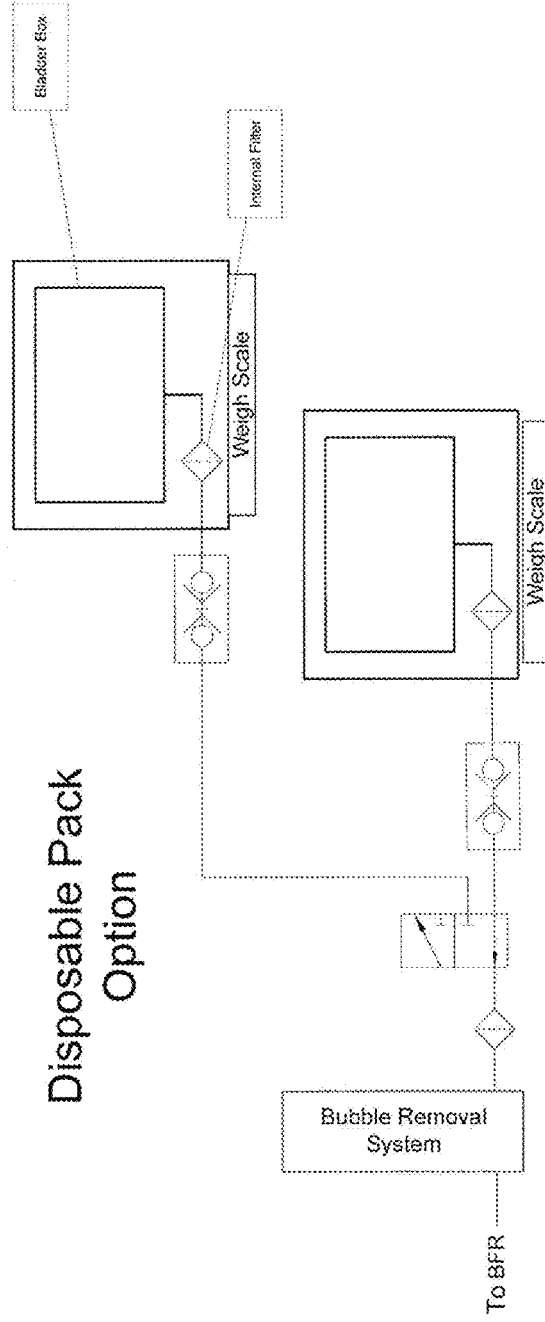

AUTOMATED SYSTEM AND METHOD OF TREATING TISSUE SAMPLES ON SLIDES

CROSS REFERENCE TO RELATED APPLICATIONS

This is a National Stage of International Application No. PCT/AU2012/001413 filed Nov. 15, 2012, claiming priority based on U.S. Provisional Patent Application No. 61/560,559 filed Nov. 16, 2011, the contents of all of which are incorporated herein by reference in their entirety.

TECHNICAL FIELD

The present invention relates to an automated system and method of treating one or more tissue samples disposed on slides. The present invention is of particular, but not exclusive, application in treating the tissue samples using a plurality of reagents to stain the tissue samples.

BACKGROUND

Existing tissue sample treatment methods, in some applications, comprise a number of steps that are performed manually. For example, in immunologic applications, such as in-situ hybridization (ISH) and immunohistochemical (IHC) applications, some steps including dewaxing and target retrieval are performed manually by an operator to treat the tissue sample before it can be used in a staining apparatus for staining the tissue sample according to a predetermined staining protocol. In this example, tissue samples are preserved in formalin and presented on microscope slides with a layer of paraffin wax protecting the sample. Thus, treatment in the form of at least dewaxing by heat and/or use of reagent is required to be performed by the operator on the slide before treatment in the form of staining of a sample can take place. Dewaxing is typically achieved by the operator manually dunking the slide in a dewaxing solution (e.g. a dewaxing reagent) to prepare the sample for staining. Also, the sample may be further treated by manually immersing the slide in another reagent, such as alcohol, to dehydrate the sample before staining can take place. In any event, the dewaxed sample on the slide is typically loaded into the staining apparatus by the operator for staining and is later retrieved by the operator after the staining process has been completed for viewing by, say, a pathologist.

Attempts have been made to automatically treat tissue samples disposed on slides for immunologic applications using, for example, an automated tissue sample staining apparatus. In this example, the automated staining apparatuses treat tissue samples using reagents to treat the sample before staining the samples on the slides. The treatment of the samples is also typically performed automatically by one or more robots configured to dispense reagents to the samples on the slides in a predetermined sequence according to a staining protocol. In addition, the robots can also be configured to dispense reagents such as dewaxing solution and alcohol to treat the samples on slides before and after staining. The reagent currently being dispensed by one of the robots, however, must be purged from the robots before other reagents can be dispensed causing delay, reagent wastage and inefficient use of the automated staining apparatus.

SUMMARY

According to one aspect of the present invention there is provided an automated system for treating one or more tissue samples disposed on slides, the system comprising:

a controller;

a plurality of slide treatment modules arranged to receive ones of the slides;

at least one fluid dispensing robot configured by the controller to dispense a plurality of reagents to said ones of the slides received in the slide treatment modules via an output nozzle disposed on the at least one fluid dispensing robot to treat said one or more tissue samples respectively; and at least one pumping means for pumping said reagents to the output nozzle of the at least one fluid dispensing robot from a plurality of reagent containers comprising said reagents; wherein the at least one fluid dispensing robot is configured by the controller to dispense said reagents in a predetermined sequence for each of the slide treatment modules to treat the one or more tissue samples disposed on each of the slides independently.

In an embodiment, the at least one fluid dispensing robot comprises at least one bulk fluid robot (BFR) configured by the controller to dispense the plurality of reagents to said ones of the slides received in the slide treatment modules via an output nozzle disposed on the at least one BFR to treat said one or more tissue samples respectively.

In an embodiment, the at least one pumping means comprises a plurality of pumping means, each of said pumping means associated with each of the plurality of reagents respectively for pumping said reagents to the output nozzle of the at least one BFR from the plurality of reagent containers comprising said reagents and a plurality of reagent lines associated with each of the plurality of reagents which extend from each of the reagent containers via the respective pumping means to the at least one BFR.

In an embodiment, the at least one BFR comprises two or more BFRs and the plurality of pumping means comprises pumping means associated with each of the plurality of reagents and with each of the BFRs.

In an embodiment, the at least one fluid dispensing robot comprises a fluid transfer probe (FTP) robot configured by the controller to dispense a plurality of high value reagents to said ones of the slides received in the slide treatment modules via an FTP nozzle disposed on the FTP robot to treat said one or more tissue samples respectively.

In an embodiment, the at least one BFR and/or the FTP robot are configured by the controller to dispense said reagents and/or said high value reagents in said predetermined sequence to stain said one or more tissue samples disposed on each of the slides independently according to a predetermined staining protocol. It will be appreciated by those persons skilled in the art that the predetermined sequences and the predetermined staining protocol are stored in a memory accessible by the controller. Thus, each slide in the slide treatment modules can be processed independently according to allocated predetermined staining protocols.

In another embodiment, the BFR and/or the FTP robot are configured to dispense said reagents to otherwise treat the samples and/or the slides by washing, dehydrating, etc. Thus, for example, the system can be used with respect to immunohistochemistry (IHC), in-situ hybridization (ISH), fluorescent in-situ hybridization, staining, microarray, and other chemical and biological applications. Also, the system can be used with respect to in-situ polymerase chain reaction (PCR).

In an example, the reagents dispensed by the BFR are bulk fluid reagents such as oxalic acid, sulphuric acid, potassium permanganate, alcohol, dewaxing agent, haematoxylin, peroxide, citric acid, EDTA, blueing agents, DI water, and Bond™ wash. The high value reagents comprise, for example, chromagens, ISH probes, fluorescents, IHC probes, antibodies, PCR reagents.

It will be appreciated by those persons skilled in the art that more than one BFR output nozzle and more than one FTP nozzle may be used by the BFR and the FTP robot respectively to dispense different reagents. In addition, it will be appreciated that the BFR output nozzle and/or the FTP nozzle has more than one nozzle. For example, in an embodiment the BFR output nozzle comprises six nozzles for dispensing different reagents to the slides independently. In this way six reagent lines are primed and can be used by different the slide treatment modules.

In an embodiment, the FTP and/or the BFR are configured by the controller to create agitation of the tissue samples disposed on the slides in each of the slide staining modules.

In an embodiment, the FTP robot comprises a first syringe pumping means and a second syringe pumping means arranged to aspirate and dispense said high value reagents to/from the FTP nozzle from a plurality of high value reagent containers comprising said high value reagents according to said predetermined sequence. In another embodiment, the FTP robot comprises a gear pump arranged to pump said high value reagents to the FTP nozzle.

In an embodiment, the first syringe pumping means and the second syringe pumping means are disposed in series and comprise bypass valves operable such that the first and the second syringe pumping means are arranged to aspirate and dispense said high value reagents independently. In another embodiment, the first syringe pumping means and the second syringe pumping means are disposed in parallel such that the first and the second syringe pumping means are arranged to aspirate and dispense said high value reagents independently.

In an embodiment, the first syringe pumping means comprises a smaller pump capacity than the second syringe pumping means. In an arrangement, the first syringe pumping means comprises a 250 µl pump capacity and the second syringe pumping means comprises a 2.5 ml pump capacity. In an embodiment, the first syringe pumping means aspirates and dispenses from 1 µl to 25 µl. In an embodiment, the first syringe pumping means aspirates and dispenses from 5 µl to 20 µl. In an embodiment, the second syringe pumping means aspirates and dispenses from 100 µl to 500 µl. In an embodiment, the second syringe pumping means aspirates and dispenses from 150 µl to 250 µl. It will be appreciated by those persons skilled in the art that other arrangements of pump capacity are envisaged to dispense different amounts of high value reagents according to different staining protocols.

In an embodiment, the FTP robot is further configured by the controller to dispense the plurality of reagents from the plurality of reagent containers via the FTP nozzle. In one arrangement, the first syringe pumping means and the second syringe pumping means are arranged to aspirate and dispense said reagents to the FTP nozzle from the reagent containers comprising said reagents. In another arrangement, the FTP robot is configured to dispense DI water to treat the sample from the same DI water container used by the BFR. In another example, a further DI water container is dedicated for use by the FTP robot. In yet another example, the FTP nozzle is disposable for reagents and tests that are at risk from cross contamination, which is especially relevant for PCR.

In an embodiment, the system further comprises a wash pump for pumping wash fluid from a wash fluid container to the FTP robot to wash the first and the second syringe pumping means of residual high value reagent that has been dispensed.

In an embodiment, the FTP robot is further configured by the controller to move said slides from an input buffer module to the slide treatment modules using a transport device (such as a suction device or gripper) disposed on the FTP robot to releasably hold the slides. It will be appreciated by those persons skilled in the art that other transport devices may be utilized to releasably hold and displace slides. In one arrangement, the FTP robot is configured by the controller to move in the x, y, z and θ (theta) axes. It will be appreciated by those persons skilled in the art that the robot can also be configured to move in even more degrees of freedom, such as six degrees of freedom, to move slides and to dispense reagents. In another arrangement, the BFR is configured by the controller to move in only the x and y axes. For example, in use, the BFRs do not move in the z axes so that they do not interfere with the movement of the FTP robot and the slides.

For example, the suction device includes a suction cup or a bellowed suction cup. It will be appreciated by those persons skilled in the art, however, that the slide transport device also includes other devices to releasably hold the slides, such as a gripper, that may have a hook arranged to grasp and lift a predisposed hooking point on a slide for, say, slides dedicated to a particular slide treatment apparatus. It will also be appreciated that the slide transport device is adjustable to cater for differently dimensioned slides or variations in the surface of a slide, such as a variation resulting from an incorrectly or damaged slide label.

In an embodiment, the FTP robot is further configured by the controller to move said slides from the slide treatment modules to an output buffer module.

In an embodiment, the slides are disposed in one or more slide racks in the input and the output buffer modules and the FTP robot is further configured by the controller to move the slides between the slide racks in the input and the output buffer modules and the slide treatment modules. For example, in use, the slides are disposed in a vertical orientation in the slide racks and are moved by the FTP to the slide treatment modules to be disposed in a horizontal orientation. Thus, in use, the FTP robot grips a slide vertically disposed in the slide rack in the input buffer module, rotates it to horizontal and places it in the slide treatment module. After treatment (e.g. staining) in the slide treatment module, the slide is gripped by the FTP robot and rotated to vertical again for placement in another slide rack in the output buffer module. In addition, the vertically disposed slides in the slide rack can be moved (e.g. dunked) in a dewaxing module of the system by the FTP robot before the FTP robot grips a particular slide in the slide rack and places it in the slide treatment module for treatment.

These slides racks thus, in use, allow for mass processing of the slides such as dewaxing, baking, and storing and for sorting of slides according to their intended treatment. For example, the samples disposed on the slide racks are all heated to a designated temperature (e.g. between 37° C. and 80° C.) in the baking module before undergoing the same staining protocol. For example, the designated temperature may be 60° C. or 37° C. for all the slides. In addition, the slide racks also allow for mass movement of slides to, for example, a coverslipping module for coverslipping the slides.

In an embodiment, the FTP robot is further configured by the controller to move said slides in the slide racks between the input and the output modules and further modules for treating the one or more tissue samples disposed on the slides using the transport device (e.g. gripper) to releasably hold (e.g. grip) the slide racks. For example, the system further comprises a slide scanning module, dewaxing module (e.g. dewax bath), cover slipper module, and a polymerase chain reaction (PCR) module (if required). It will be appreciated by those persons skilled in the art that further modules are envisaged for treating the slides. In any event, the FTP robot is configured to move the slides between the modules in a predetermined and optimised sequence. In one arrangement, the gripper comprising a hook arranged to grasp and lift the slide rack at a designated hooking point disposed on the slide rack. In any case, it will be appreciated by those persons skilled in the art that other gripping or grasping means are envisaged to move the slide racks.

In an embodiment, the FTP robot is further configured by the controller to move said slide racks between the input and the output modules and the further modules.

In an embodiment, the system further comprises cooling means for cooling at least some of the reagent containers and the high value reagent containers. In the embodiment, the cooling means comprises a cooling plate disposed beneath reagent containers requiring cooling. In another arrangement, the cooling means comprises a refrigerator module arranged to control the temperature of the reagents in the reagent containers stored therein. In another embodiment, the system further comprises heating means for heating at least some of the reagent containers and the high value reagent containers. In this embodiment, the heating means comprises a heating plate disposed beneath reagent containers requiring heating. Alternatively, the heating means may comprise heater pads, RF, microwave, and convection means and the cooling means may comprise chilling means, fins and/or a Peltier effect cooler. In yet another embodiment, the heating and/or cooling plates are disposed at (e.g. beneath) the slide treatment modules to heat/cool the slides having reagent dispensed thereon. Furthermore, it is envisaged that the temperature of the heated/cooled slide is configurable by the controller.

In an embodiment, the input and the output buffer modules have the ability to receive at one time up to 200 slides disposed on 10 slide racks. It will be appreciated by those persons skilled in the art that other slide rack and buffer module configurations may be used by the system, such as slide racks holding only 10 slides each and the input and the output buffer modules having the ability to receive, say, 30 slide racks for improving slide density of the system and the relative size of the input and output buffers.

In some embodiments, the input buffer modules may also function as the output buffer modules and vice versa; for example, a slide (e.g. substrate) removed from the input buffer for treatment may then be returned to the same location in the buffer module after treatment for removal from the buffer module. That is, the same module can be used to introduce slides to the system and to remove slides from the apparatus. In the example, the input buffer may then cure the slides after coverslipping.

Preferably, grouping of slides (or substrates) is performed according to any desired configuration including, but not limited to, common patient case, marker batch, staining batch, specialized protocol, referring doctor, destined pathologist, or other preferred management configuration. In one or more embodiments, grouping of substrates may be configurable by the user according to desired groupings and/or preferences.

In an embodiment, the system comprises at least one treatment zone for baking, staining, coverslipping, molecular testing (for example polymerase chain reaction), scanning and/or curing of coverslip adhesive. In the embodiment, the treatment zone may be utilized as a standalone feature wherein the user may utilize their preferred feature, for example baking or coverslipping, without requiring the utilization of other or all features of the treatment zone.

In an embodiment, the system further comprises sensing means for sensing amount of said reagents dispensed by the or each of said BFRs and/or amount of said high value reagents dispensed by the FTP robot. In an arrangement, the sensing means sense dispensed reagent amount for each of the reagent containers and the high value reagent containers. In an example, the controller compares the sensed amount of reagent used from the container to determine whether the correct amount of reagent has been dispensed. In a further example, the controller provides an indication or instruction to order a reagent when that reagent container is sensed to be nearing empty. In another example, sensing means (e.g. sensors) are disposed in the slide treatment modules and at the FTP robot or BFR to compare the amount of reagent dispensed with that on the slide, such as by comparing pressure differential, to confirm delivery.

In one or more embodiments, sensing for dispensed reagent amounts may also be performed using sensing means configured to use liquid level sensing technologies such as probe touch technology and/or by monitoring changes in capacitance or pressure at the FTP nozzle tip. Alternatively, optical liquid level sensing systems and/or ultrasonic systems may be employed. Measurements of reagent volumes taken at the FTP nozzle, in a chamber and/or through the outlet of the FTP, can be compared by the controller to cross check against the total volume dispensed according to the number of protocols performed for each of the slide treatment modules. This cross check can then be used for inventory control of reagents stored by the system. In addition, this cross check can be used by the controller to process the slides in a deterministic manner by confirming that the treatment (e.g. the slide staining protocol) has been completed correctly. The controller is thus arranged to receive information such as incubation times in the baking or staining modules, and delivery and removal of the right reagents in the correct sequence in addition to sensed reagent use.

In an embodiment, the system further comprises a waste treatment module arranged to treat waste from treating said one or more tissue samples using one or more of said reagents. For example, potassium permanganate, sulphuric acid, ascorbic acid, H2O2, peroxidase and oxalic acid can be used to treat waste from the staining of tissue samples. In addition, the system further comprises a boiler to neutralise biological hazards by boiling or by filtration. In any case, the treated waste can then be disposed of in a conventional fashion, such as by being plumbed into a sink, thus reducing hazardous waste handling and waste disposal costs. Furthermore, it is envisaged that hazardous waste and non-hazardous are separated by the waste treatment module According to another aspect of the present invention there is provided an automated method of treating one or more tissue samples disposed on slides, the method comprising:
  receiving ones of the slides in a plurality of slide treatment modules;
  pumping a plurality of reagents to an output nozzle of at least one fluid dispensing robot from a plurality of reagent containers comprising said reagents using at least one pumping means; and
dispensing the plurality of reagents to said ones of the slides received in the slide treatment modules via the output nozzle disposed on the at least one fluid dispensing robot in a predetermined sequence for each of the slide treatment modules thereby treating the one or more tissue samples disposed on each of the slides independently.

According to another aspect of the present invention there is provided an automated tissue sample treatment apparatus for treating one or more tissue samples disposed on slides, the apparatus comprising:

a plurality of slide treatment modules arranged to receive ones of the slides;

at least one fluid dispensing robot configured by the controller to dispense a plurality of reagents to said ones of the slides received in the slide treatment modules via an output nozzle disposed on the at least one fluid dispensing robot to treat said one or more tissue samples respectively; and at least one pumping means for pumping said reagents to the output nozzle of the at least one fluid dispensing robot from a plurality of reagent containers comprising said reagents; wherein the at least one fluid dispensing robot is configured by the controller to dispense said reagents in a predetermined sequence for each of the slide treatment modules to treat the one or more tissue samples disposed on each of the slides independently.

According to another aspect of the present invention there is provided computer program code which when executed implements the above described method.

According to another aspect of the present invention there is provided a tangible computer readable medium comprising the above program code.

According to another aspect of the present invention there is provided a data file comprising the above program code.

BRIEF DESCRIPTION OF THE DRAWINGS

Embodiments of the present invention will now be described, by way of example only, with reference to the accompanying drawings, in which:

FIG. 7 is a schematic view of a reagent container of the system of FIG. 5;

FIG. 8 is a schematic view of two reagent containers of the system of FIG. 5;

DETAILED DESCRIPTION

Figure 1:
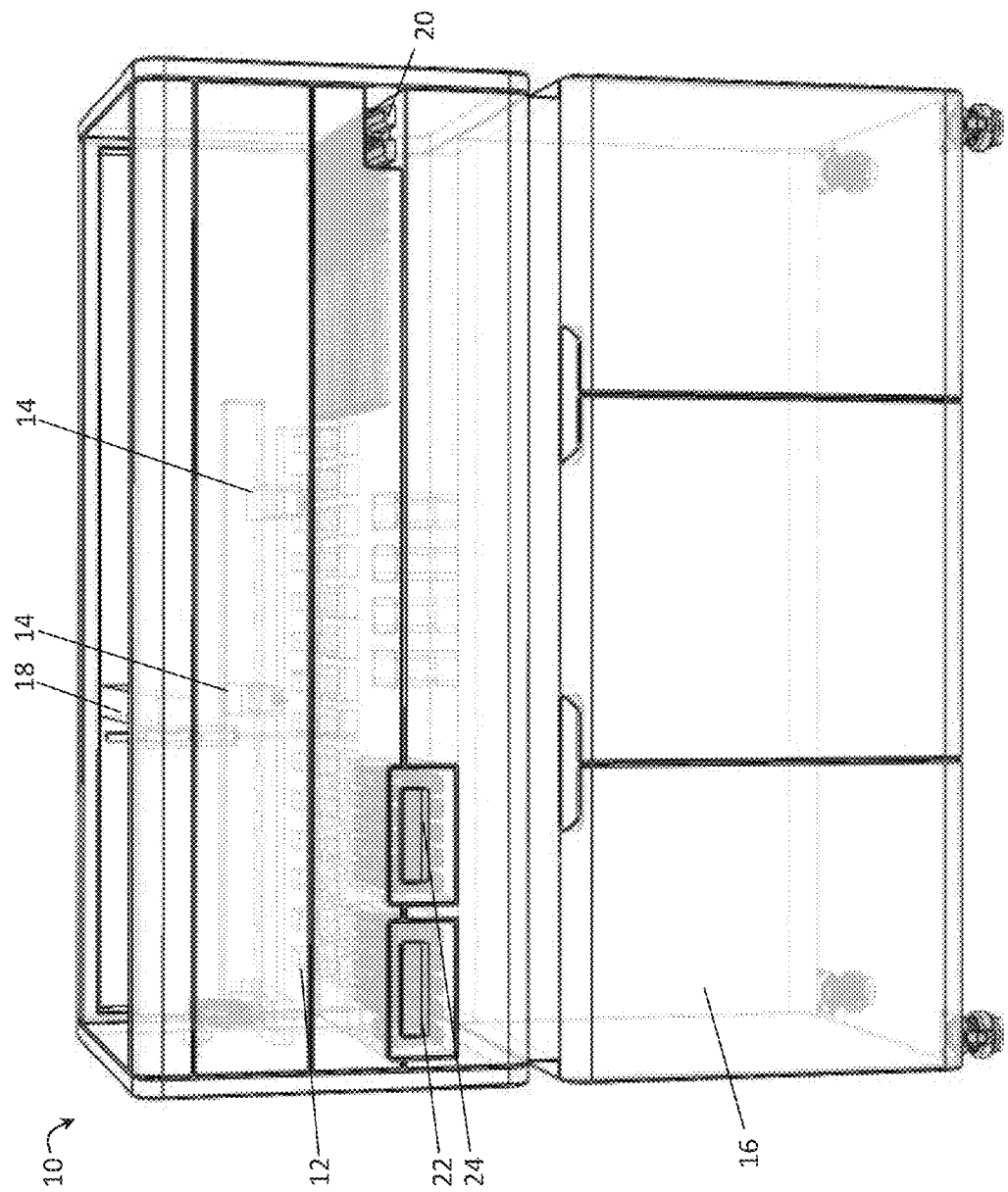
FIG. 1 is a perspective view of an automated slide treatment apparatus according to an embodiment of the present invention.

An automated tissue sample treatment apparatus 10 for treating one or more tissue samples disposed on slides according to an embodiment of the present invention is shown in FIG. 1. In this embodiment, the apparatus 10 and, indeed, the system of treating a tissue sample as described above, includes a controller (not shown in this figure). However, it will be appreciated by a person skilled in the art that in other embodiments the controller is implemented remotely from the apparatus 10.

The apparatus 10 also includes a plurality of slide treatment modules 12 arranged to receive ones of the slides and a fluid dispensing robot in the form of at least one bulk fluid robot (BFR) 14 configured by the controller to dispense a plurality of reagents stored in reagent containers to the slides received in the slide treatment modules 12 via an output nozzle disposed on the BFRs to treat tissue samples on the slides. In the embodiment shown in FIG. 1, there are two BFRs 14 configured by the controller to dispense reagents to the slides, such as oxalic acid, sulphuric acid, potassium permanganate, alcohol, dewaxing agent, haematoxylin, peroxide, citric acid, EDTA, DI water, and Bond™ wash, to treat the tissue samples disposed thereon.

These reagents (e.g. bulk fluid reagents) are stored in reagent containers housed in the apparatus 10 and, in this embodiment, are accessible via panel 16 of the apparatus 10. The apparatus 10 also includes at least one pumping means (not shown in this figure) for pumping said reagents to the output nozzle of the BFRs 14 from the reagent containers. The BFRs 14 are configured by the controller to dispense these reagents in a predetermined sequence for each of the slide treatment modules to treat the one or more tissue samples disposed on each of the slides independently.

In an example, the apparatus 10 includes a plurality of pumping means, each of which are associated with each of the plurality of reagents respectively for pumping the reagents to the output nozzle of each BFR 14 from the reagent containers. In order for the reagents to be dispensed, the apparatus 10 includes a plurality of reagent lines (not shown in this figure) associated with each of the reagents which extend from each of the reagent containers via the respective pumping means to the BFRs 14. That is, the apparatus 10 includes dedicated pumping means (e.g. pumps) for each reagent and dedicated reagent lines extending from each reagent container via each pump to each BFR. Thus, in the example where there are ten bulk fluid reagents stored in ten different bulk fluid reagent containers and there are two BFRs 14, dedicated reagent lines extend from each of the ten containers to both BFRs 14 via twenty in-line pumps. Also, in an example, each BFR output nozzle has ten nozzles for each of the reagents. In another example, there are ten pumps associated with each container and the dedicated reagent lines extend from each of the ten pumps to both BFRs 14.

In addition, the fluid dispensing robot of the apparatus 10 further includes a fluid transfer probe (FTP) robot 18 configured by the controller to dispense a plurality of high value reagents stored in high value reagent containers 20 to the slides in the slide treatment modules 12 via an FTP nozzle 28 disposed on the FTP robot 18 to the tissue samples. Thus, in use, the BFRs 14 and the FTP robot 18 are configured by the controller to dispense bulk fluid reagents and high value reagents in a predetermined sequence to treat the tissue samples and, in one example, stain the tissue samples according to a predetermined staining protocol for in-situ hybridization (ISH) and immunohistochemical (IHC) applications. In this way, the BFRs and the FTP robot are configured by the controller to dispense reagents for each of the slide treatment modules 12 to treat (e.g. stain) tissue samples disposed on each of the slides in the modules 12 independently.

It will be appreciated by those persons skilled in the art that the high value reagent containers 20 and the bulk fluid reagent containers comprise a variety of sizes, shapes and configurations necessary to facilitate adequate supply of reagent for a single reaction or multiple reactions without requiring replacement and adequately reside within the architecture of the apparatus 10. In addition, these containers can form part of a detachable reagent system which is loaded onto the apparatus 10 utilizing a multiple reagent container support, such as a tray or carousel.

Furthermore, the FTP robot 18 is configured by the controller to move the slides in the apparatus 10 to the various modules for treating the tissue samples independently. The FTP robot 18 shown in the figures includes a gripper 26, such as a suction means, to grip a slide and move the slide from an input buffer module 22, introducing the slide to the apparatus 10 for treatment, to the slide treatment modules 12, so that the sample can be treated, and then to an output buffer 24 for subsequent removal of the slide from the apparatus 10. To do so, the FTP robot 18 is configured by the controller to move in the x, y, z and θ (theta) axes. Also, the BFRs 14 are configured by the controller to move in the x, y and z axes so that they do not interfere with the movement of the slides by the FTP robot 18.

As described, in one embodiment, the gripper 26 is a bellowed suction cup, which allows for the further application of friction than a standard suction cap. The suction cup may be made from a material such as polymeric, elastomeric or plastic material such as nitrile, polyurethane or viton and it may include internal cleats to ensure the slide is held in place. It will be appreciated by those persons skilled in the art that the bellowed suction cup includes a vacuum means for activating the cup that is configured by the controller to releasably hold the slides. Also, the vacuum means may be configured to operate with the use of pressure sensors to maintain pressure and thus grip on the slides. In one embodiment, the vacuum means maintains a positive pressure to avoid the slide sticking to the bellow suction cup.

Figure 2:
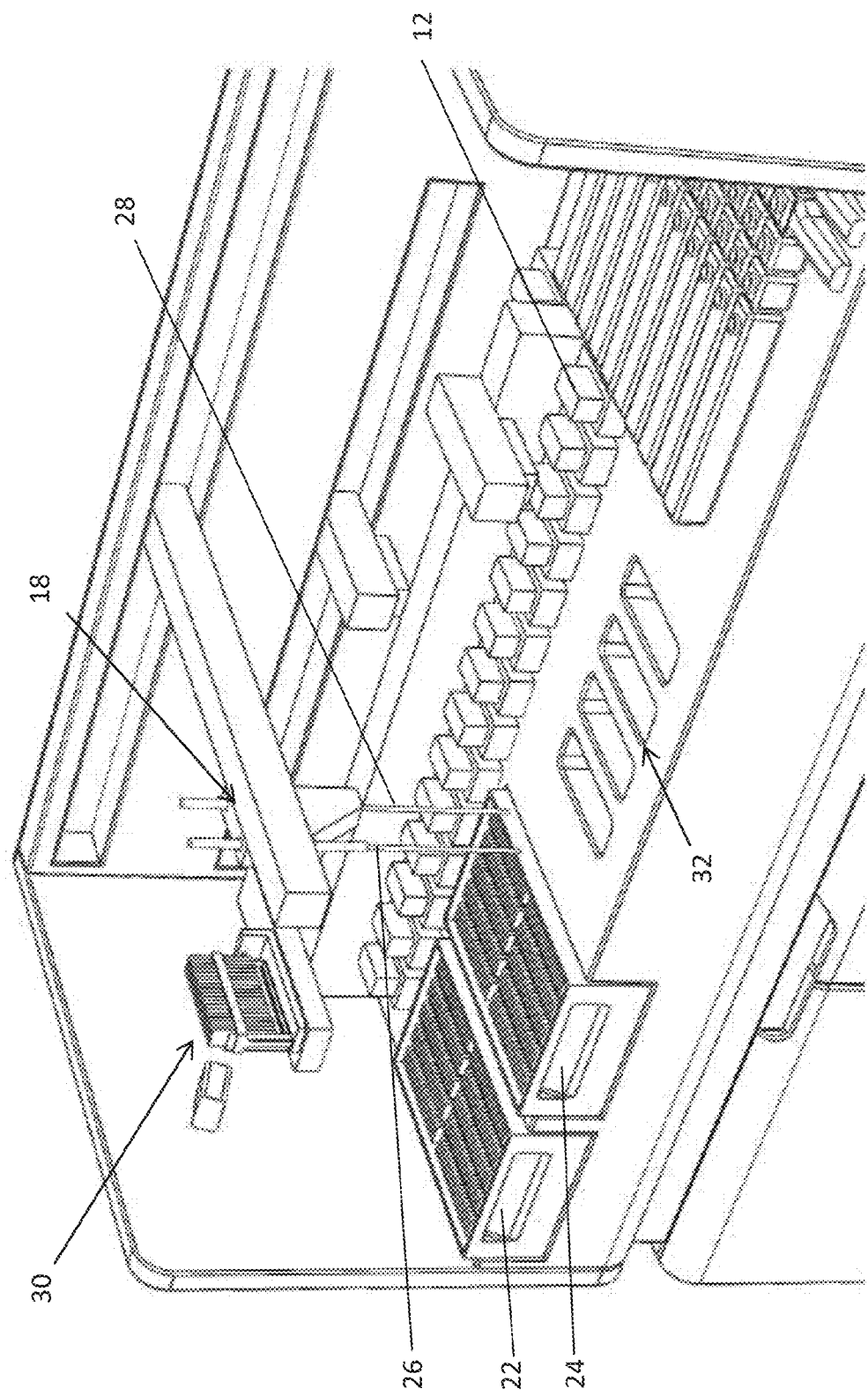
FIG. 2 is a further perspective view of the automated slide treatment apparatus of FIG. 1.
Figure 3:
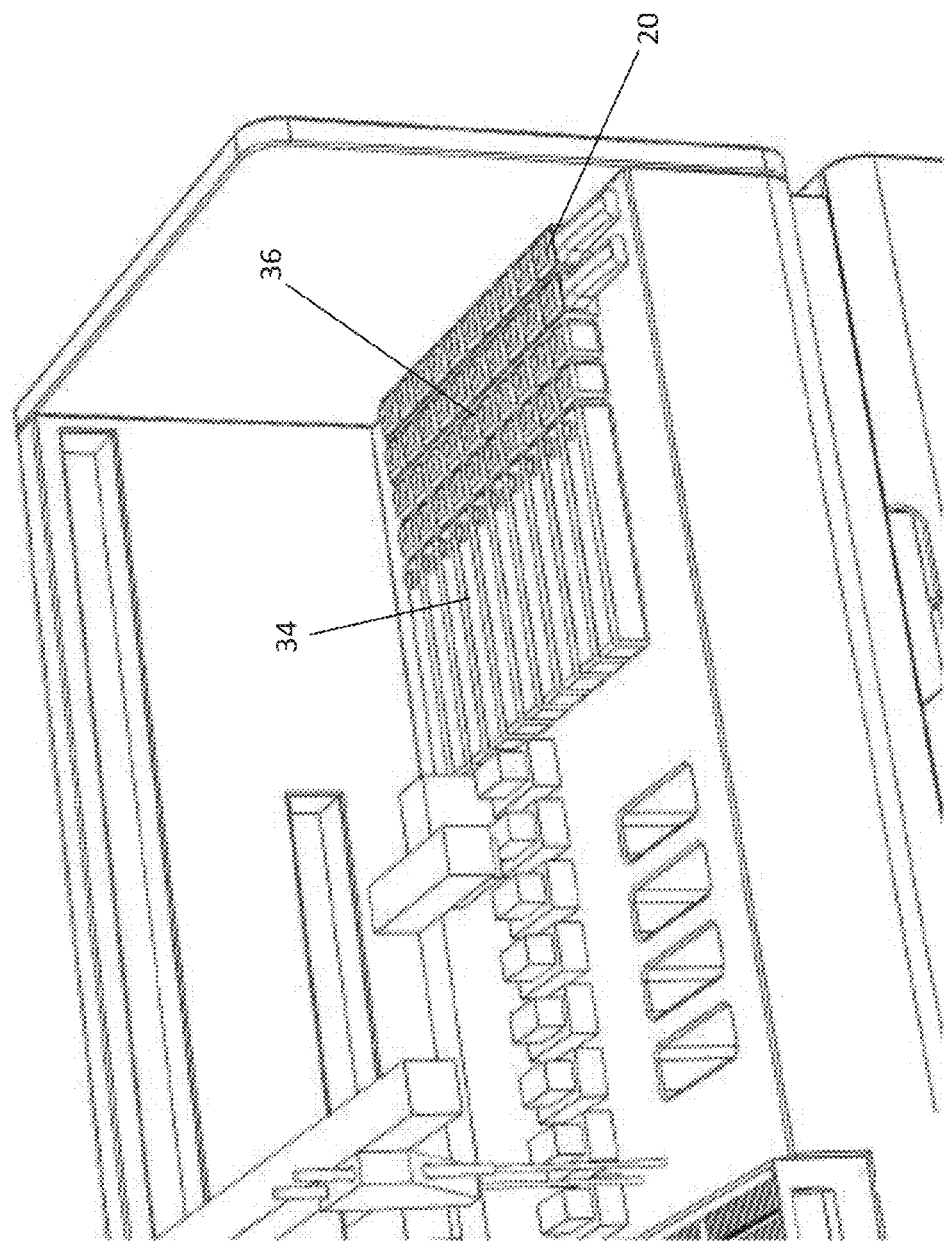
FIG. 3 is a further perspective view of the automated slide treatment apparatus of FIG. 1.

FIGS. 2 and 3 show the automated tissue sample treatment apparatus 10 in more detail. It can be seen that the input 22 and the output buffer 24 modules comprise a number of slide racks of slides disposed vertically therein. The FTP robot 18 is thus configured by the controller to move the slides between the slide racks in the input 22 and the output buffer 24 modules and the slide treatment modules 12. In the figures, the slides are disposed in a vertical orientation in the slide racks and are moved by the FTP robot 18 to the slide treatment modules 12 to be disposed in a horizontal orientation for treatment. Thus, the FTP robot 18 is configured to grip a slide vertically disposed in the slide rack in the input buffer module 22 using the gripper 26, rotate (theta axis) it to horizontal and place it in the slide treatment module 12 whilst moving in the x, y and z axes. After treatment, including staining, in the slide treatment module 12, the slide is again gripped by the gripper 26 of the FTP robot 18 and rotated (theta axis) to vertical for placement in another slide rack in the output buffer module 24. In this way, an operator can introduce slides to the apparatus 10 for treatment without disturbing operation of the FTP robot 18 and the BFRs 14 as well as remove slides from the apparatus 10. Alternatively, drawers for accessing the slides may be locked during removal and/or replacement of slides. It will be appreciated that the FTP robot 18 is configured by the controller to rotate a slide from being vertically disposed to being horizontally disposed in a number of ways. One way is for the gripper 26 to be disposed at the end of a rotating member disposed at 45 degrees to the z axis or vertical axis so that rotation of the rotating member about the θ axis will rotate the slide from being vertically disposed to being horizontally disposed and vice versa.

The slides in the slide rack can also be moved by the FTP robot 18 to other modules in the apparatus 10 including a slide scanning module 30 to read a bar code associated with each slide and/or slide rack, a baking and curing module (not shown), and a bath module 32 in which racks of slides (or individual slides) are dunked in a dewaxing or washing bath of the bath module 32 by the FTP robot 18. It will be appreciated by those persons skilled in the art that other baths of reagents can be used by the apparatus 10 to treat the slides, such as DI water and alcohol. Also, it is appreciated that the gripper 26 is arranged to grip the slide racks so that the FTP robot 18 can move them between modules for processing. Also, while not shown, a coverslipper module can be implemented by the apparatus 10 to apply a cover to slides (e.g. a glass or tape cover slip) after treatment of the samples on the slides. It will also be appreciated by those persons skilled in the art that the various modules may be deployed removeably with respect to the apparatus 10. For example, in some instances, the coverslipper module is not required and is not deployed with the apparatus 10.

It will also be appreciated that machine readable identifier(s), for example bar codes, may be located at any site on the apparatus 10, such as reagent containers, slides, slide mountants, coverslip magazines, cover members, or any other such location, to facilitate identification, inventory control or otherwise manage or control components or processes of the apparatus 10.

Figure 9:
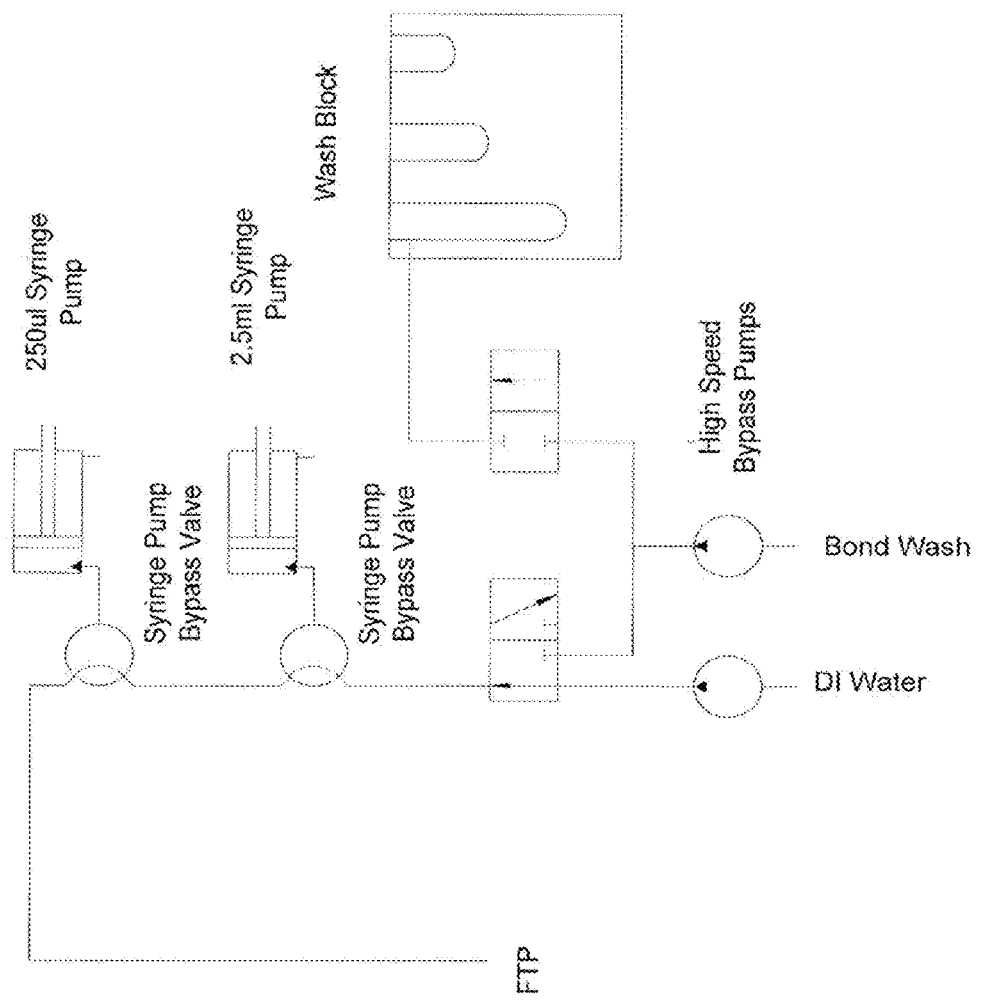
FIG. 9 is a schematic view of a fluid transfer probe (FTP) robot of the system of FIG. 5.

It can also be seen from FIGS. 2 and 9 that the FTP robot comprises a first syringe pumping means and a second syringe pumping means arranged to pump independently high value reagents to an FTP nozzle 28 from high value reagent containers 20 containing these high value reagents. In an example, the first syringe pumping means comprises a first syringe pump with a 250 µl pump capacity and the second syringe pumping means comprises a second syringe pump with a 2.5 ml pump capacity. In this way, the smaller syringe pump is arranged to dispense and aspirate smaller volumes (e.g. less than 20 µl) of high value reagents, such as chromagens, or components for mixing, or antibodies, while the larger syringe pump is arranged to dispense and aspirate larger volumes of high value reagents which can be dispensed onto, say, multiple slides. Thus, wastage of high value, less used reagents is reduced by having the smaller syringe pump aspirate and dispense the required amount to the desired slide while the larger pump can dispense more commonly used high value reagents to a larger number of slides. Also, in this way, the FTP robot 18 is required to make fewer movements by dispensing the more commonly used high value reagents to the different slides. It will be appreciated by those persons skilled in the art that the first and second syringe pumps have sufficient flow to perform mixing in a chamber of the FTP robot 18 when aspirating from the high value reagent containers.

Moreover, the first and second syringe pumps are arranged in series with the smaller pump closer to the FTP output nozzle 28 and each syringe pump having bypass valves so that the pumps can be used independently. In addition, both pumps can be bypassed so that the FTP robot 18 reagent lines can be washed using DI water or Bond™ wash pumped via a wash pump.

Figure 4:
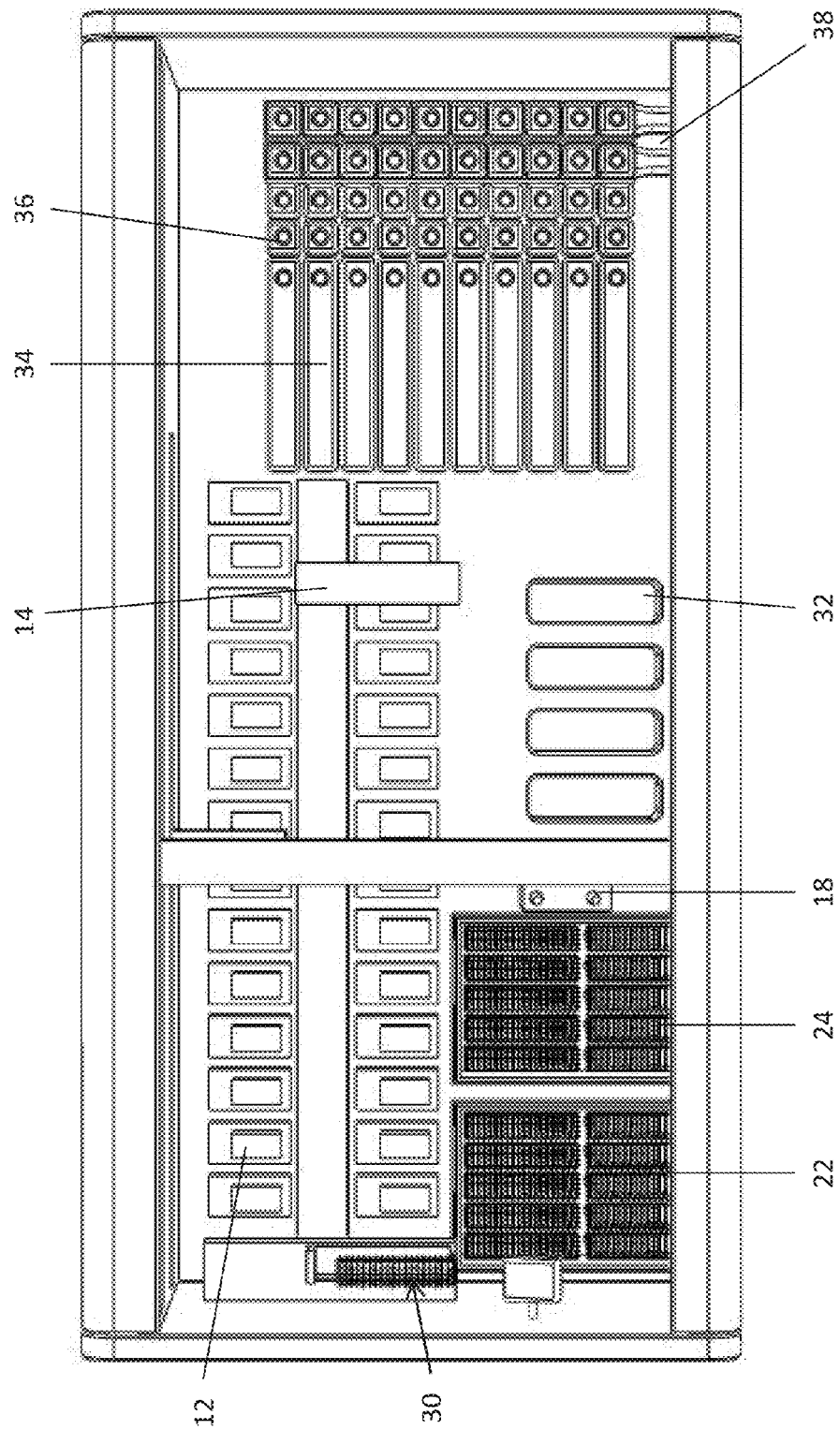
FIG. 4 is a plan view of the automated slide treatment apparatus of FIG. 1.

FIGS. 3 and 4 also show the high value reagent containers 20 in more detail. Here it can be seen that high value reagents, or components for mixing, are typically dispensed with the smaller pump are stored in smaller reagent containers 36 (e.g. for antibodies) while more frequently used high value reagents (e.g. detection reagents) are stored in larger reagent containers 34. Also, the high value reagent containers 20 can be loaded into the apparatus 10 via the access means 38 without disturbing operation of the apparatus 10. It can also be seen that the syringe pumps utilise a syringe including the FTP nozzle 28 to enter into the reagent containers 34 and 36 via an opening disposed thereon to draw reagents from those containers for aspirating and dispensing by the FTP nozzle 28.

Although not shown in the figures, the high level reagents can be individually cooled or heated in their respective containers using suitable cooling or heating means, such as cool plates or hot plates disposed beneath the containers. Furthermore, in another embodiment, the apparatus 10 also includes a mixing module to mix reagents therein. In this embodiment, the FTP robot 18 is configured to aspirate reagents into a mixing module container to mix these reagents and to subsequently be dispensed to a slide. It is envisaged that the mixed reagents in the container in the mixing module can also be heated and cooled in the fashion described above. In any case, the first or second syringe pumps can then be used to dispense the mixed reagent to the desired slides.

It will be appreciated by those persons skilled in art that the controller can be either implemented in a computer housed within the apparatus 10 or can be implemented by a computer remote from the apparatus 10 (including modules residing thereon for monitoring, tracking, scheduling, protocol sequencing, selecting reagents, LIS and other connectivity interfacing, etc.) and connected thereto via a communications network, such a local area network (LAN). In any case, the controller comprises a number of modules to provide instructions to the BFRs 14 and the FTP robot 18 to control movement thereof and dispensing of reagents. In an example, the controller is configured to communicate with the sample tracking systems, such as Leica's Cerebro™ platform, to allow planning of scheduling, protocol sequencing, reagent requirements, LIS and other connectivity The controller is shown schematically in FIG. 5 as a controller 40 having a BFR module 42 configured to control movement and reagent dispensing for each BFR 14A 14N and an FTP robot module 44 to control movement and reagent dispensing for the FTP robot 18. These modules are implemented using a processor in connection with instructions stored in a memory 46 accessible by the controller 40. It will be appreciated by those persons skilled in the art that the memory 46 may reside in the computer housed in the apparatus 10 or may be hosted remote from the computer in data communication with the controller 40. In any event, the controller 40 is configured to read instructions from the memory 46 to operate the apparatus 10 to treat tissue samples on slides in each of the slide treatment modules 12. The memory 46 also includes instructions to process the slides from the input buffer 22 to the other modules in a deterministic way to optimise throughput of the slides in the apparatus 10. Also, treatment protocols, including staining protocols (e.g. order of reagents to be dispensed by the BFR and the FTP robot to the slides) are also stored in the memory 46 so that the controller 40 can configure the BFRs 14A 14N and the FTP robot 18 to dispense reagents to the slides in the slide treatment modules 12 in the required order.

Figure 14:
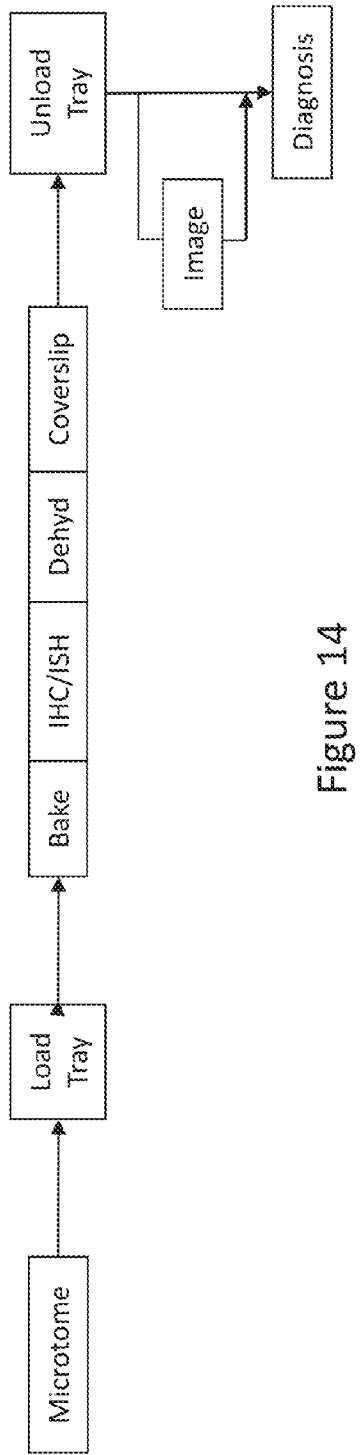
FIG. 14 is a flow chart of a method of treating one or more tissue samples according to an embodiment of the present invention.

As described, the controller 40 is configured to read instructions from the memory 46 to move and process the slides through the various modules of the apparatus 10. For example, with reference to the flow chart of FIG. 14, tissue samples are obtained by sectioning a sample tissue using a microtome and these tissue samples are placed on slides by an operator, which are then loaded onto a slide rack or tray for inserting into the apparatus 10. The controller 40 then gives instructions to the FTP robot 18, as described above, to move the slide tray and/or the slides to the various modules of the apparatus 10 in a desired order and to automatically treat the tissue samples. These modules also include a baking module (not shown) to dry the tissue sample before staining, the slide treatment modules 12 where staining (e.g. IHC/ISH) is performed, a dehydration module (e.g.an alcohol bath), and a coverslipping module. Once these modules have acted on the slides accordingly, the slides are returned to the output buffer module 24 for unloading and for subsequent imaging and diagnosing of the stained tissue samples by an operator. Furthermore, the slide sorting module 30 shown in FIG. 2 reads a barcode associated with a slide which provides instruction to the controller 40 to treat the tissue sample on that slide. For example, the instructions comprise reference to the tissue staining protocol for that slide stored in the memory 46.

Figure 5:
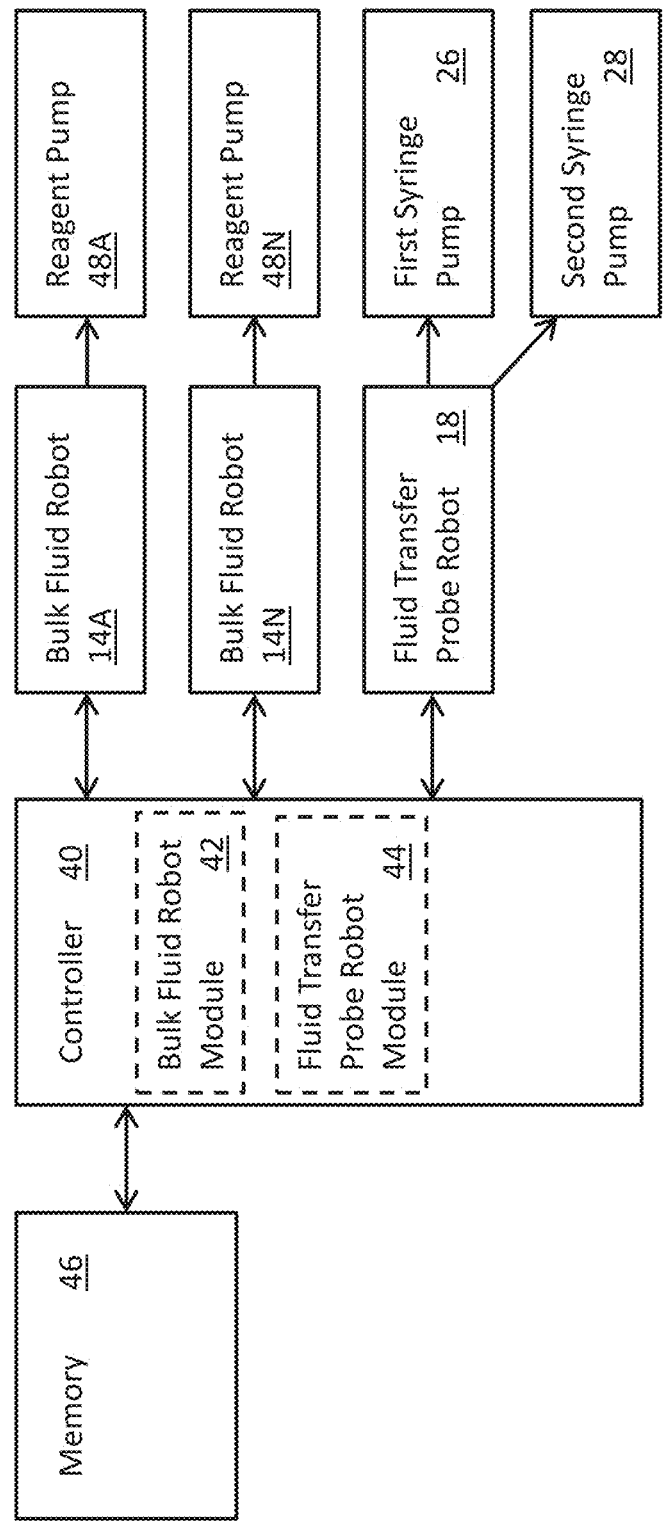
FIG. 5 is a schematic view of an automated system for treating one or more tissue samples according to an embodiment of the present invention.

In the embodiment shown in FIG. 5, the BFRs 14A 14N are configured to provide instructions to respective reagent pumps 48A 48N to dispense a predetermined amount of reagent to the slides. Also, the controller 40 is configured to provide instructions to the first syringe pump and the second syringe pump to aspirate and dispense a predetermined amount of high value reagent to the slides in a predetermined sequence of reagents.

Figure 6:
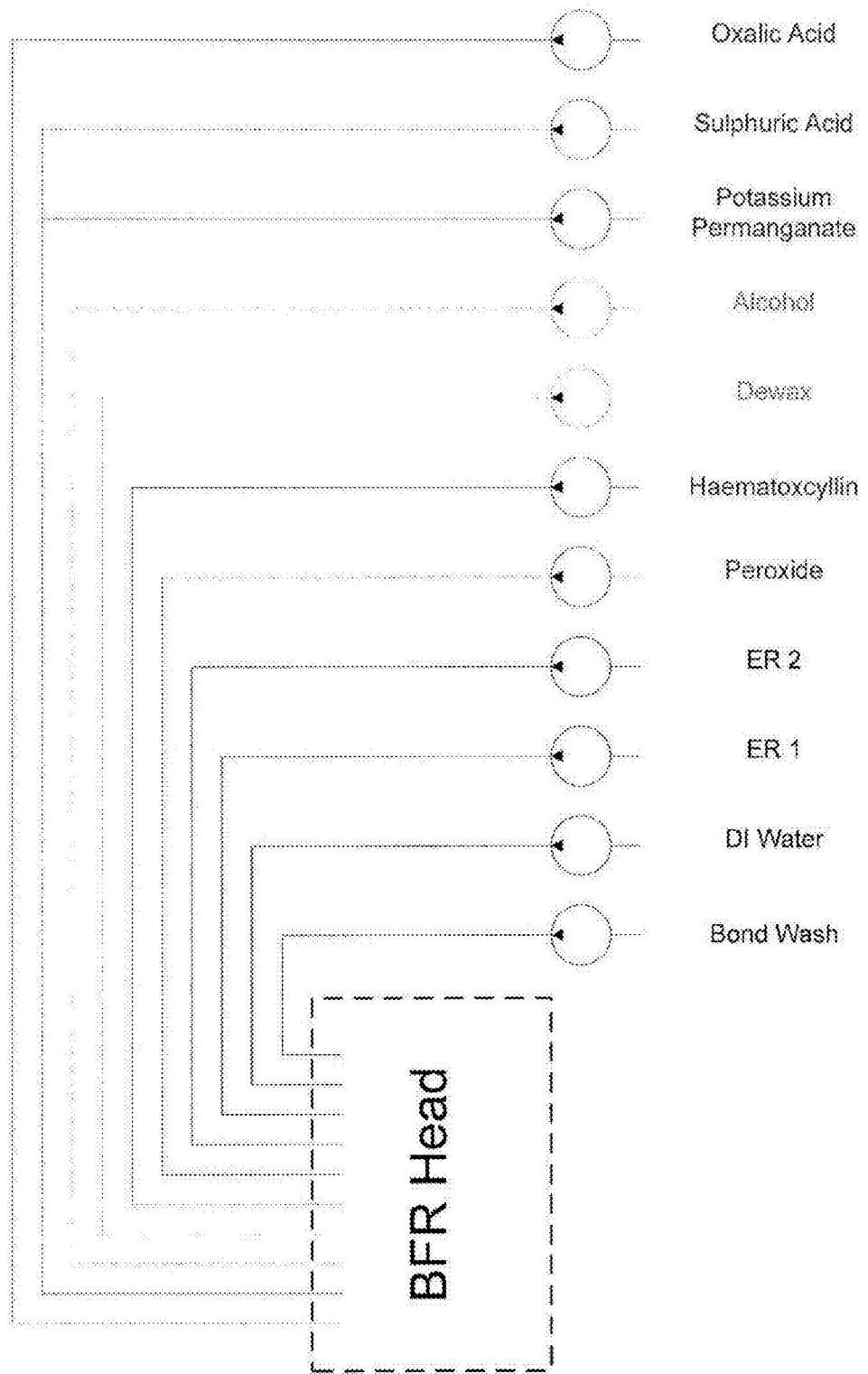
FIG. 6 is a schematic view of a bulk fluid robot (BFR) and a plurality of reagent lines of the system of FIG. 5.

Referring now to FIG. 6, a BFR head comprising the BFR output nozzle is shown schematically in connection with the pumps for each bulk fluid reagent. The reagents dispensed by the BFR are bulk fluid reagents including oxalic acid, sulphuric acid, potassium permanganate, alcohol, dewaxing agent, haematoxylin, peroxide, EDTA, citric acid, DI water, and Bond™ wash. It can be seen from this figure that each bulk fluid reagent has a dedicated reagent line extending from respective containers (not shown) via respective pumps. It will also be appreciated by those persons skilled in the art that the BFR head may comprise more than one nozzle to dispense each or combinations of these reagents.

In addition, it will be appreciated that the bulk fluid reagent containers, or bottles, can be disposed in different configurations in the apparatus 10. FIG. 7 shows a fixed container configuration where the reagent container is fixedly mounted to the apparatus 10. In this embodiment, an operator refills the fixed container via an inlet, having a strainer, on the container. In another embodiment, the bulk fluid reagent containers are disposable and are removably mounted to the apparatus 10 as shown in FIG. 8. In this way, the operator replaces the removable container when the level of reagent contained therein nears empty. In both embodiments, the apparatus 10 comprises a sensing means in the form of a weigh scale for sensing the amount of reagents dispensed by the BFRs 14. The weigh scales can also be used for diagnostic purposes for the apparatus 10, such as comparing how much reagent was determined to be used with how much was actually used. In addition, while not shown, it is envisaged that the weigh scales are also used by the apparatus 10 with respect to each high value reagent container to sense the amount of high value reagents dispensed by the FTP robot 18. Also, as described above, liquid level sensing technologies, such as capacitance, are employed in these embodiments to sense the amount of reagents dispensed by the FTP robot 18 and/or the BFRs 14. The liquid level sensing technology is incorporated to ensure continued operation by the provision of adequate levels of reagents and to notify users of impending reagent changeover, and to facilitate management of reagent use and life span.

Also, it can be seen in FIGS. 7 and 8 that each container has a pump connected thereto and the disposable container embodiment includes a bubble removal system to remove any bubbles introduced to the reagent lines by, say, inserting the containers into the apparatus 10.

Figure 10:
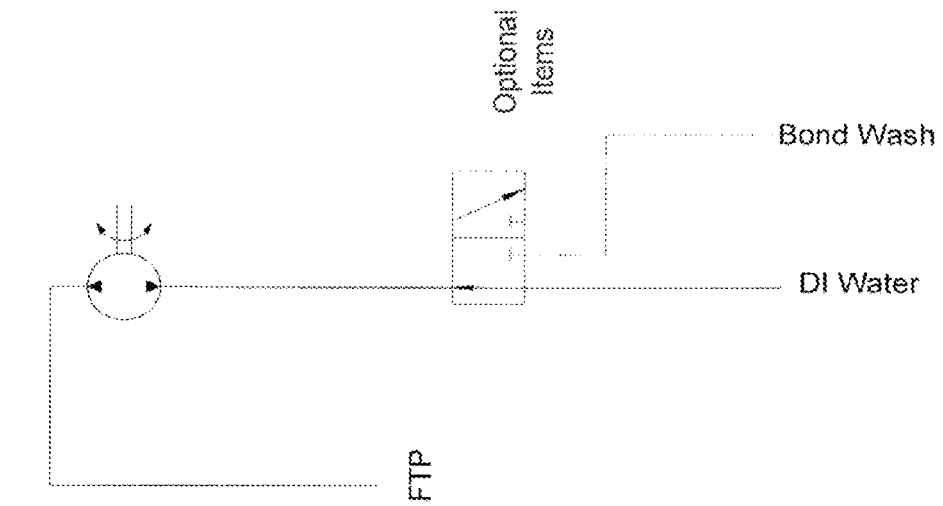
FIG. 10 is a schematic view of another fluid transfer probe (FTP) robot of the system of FIG. 5.

Furthermore, different configurations of the FTP robot 18 are envisaged and are shown in the embodiments of FIGS. 9 and 10. In FIG. 9, it can be seen that the FTP robot 18 comprises a first 250 µl syringe pump and a second 2.5 ml syringe pump connected in series as described. Also, for the two syringe pumps to be operable independently, syringe pump bypass valves are deployed by the apparatus 10. Further, to wash the lines from the FTP nozzle 28 to the pumps, a wash block is deployed in association with Bond™ wash and DI water pumps. In an embodiment, the same Bond™ wash pump and DI water pump are used as for the BFR with further reagents line to deliver these reagents to the FTP robot 18. In another embodiment, high speed diaphragm wash pumps are used by the apparatus 10 in association with a solenoid selector valve to enable selection of Bond™ wash and DI water for washing the fluid delivering lines of the FTP robot 18. In an alternative embodiment, the FTP robot 18 comprises a single gear pump rather than the syringe pumps to pump the high level reagents to the FTP robot as shown in FIG. 10.

Figure 11:
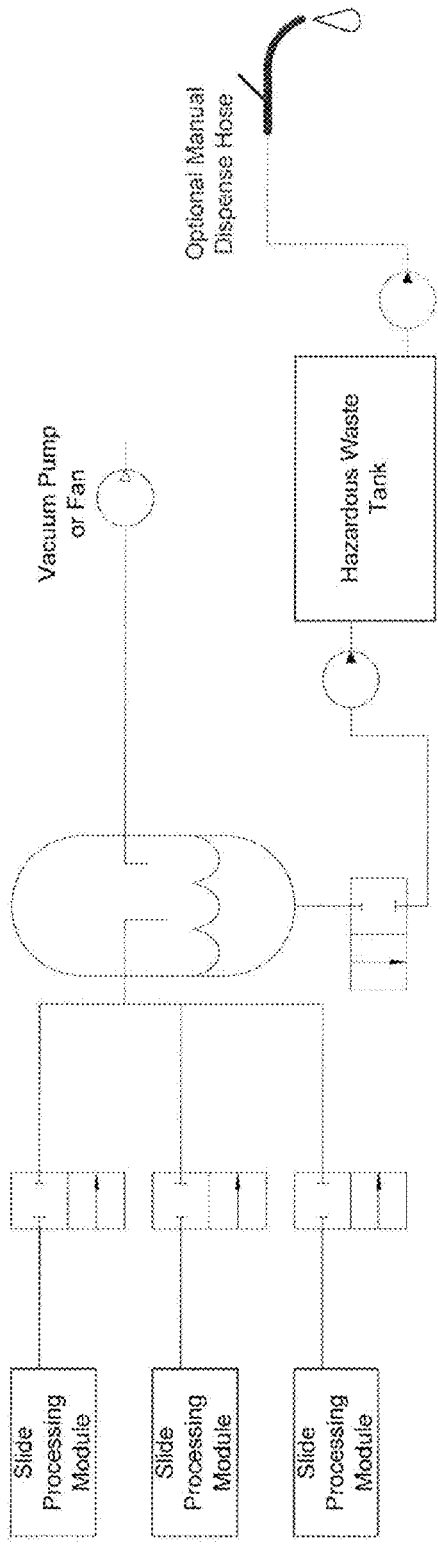
FIG. 11 is a schematic view of a waste treatment module of the system of FIG. 5.
Figure 12:
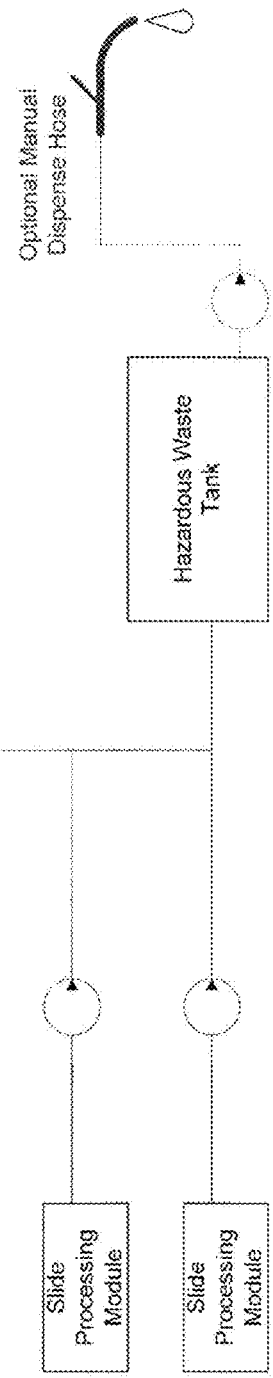
FIG. 12 is a schematic view of another waste treatment module of the system of FIG. 5.
Figure 13:
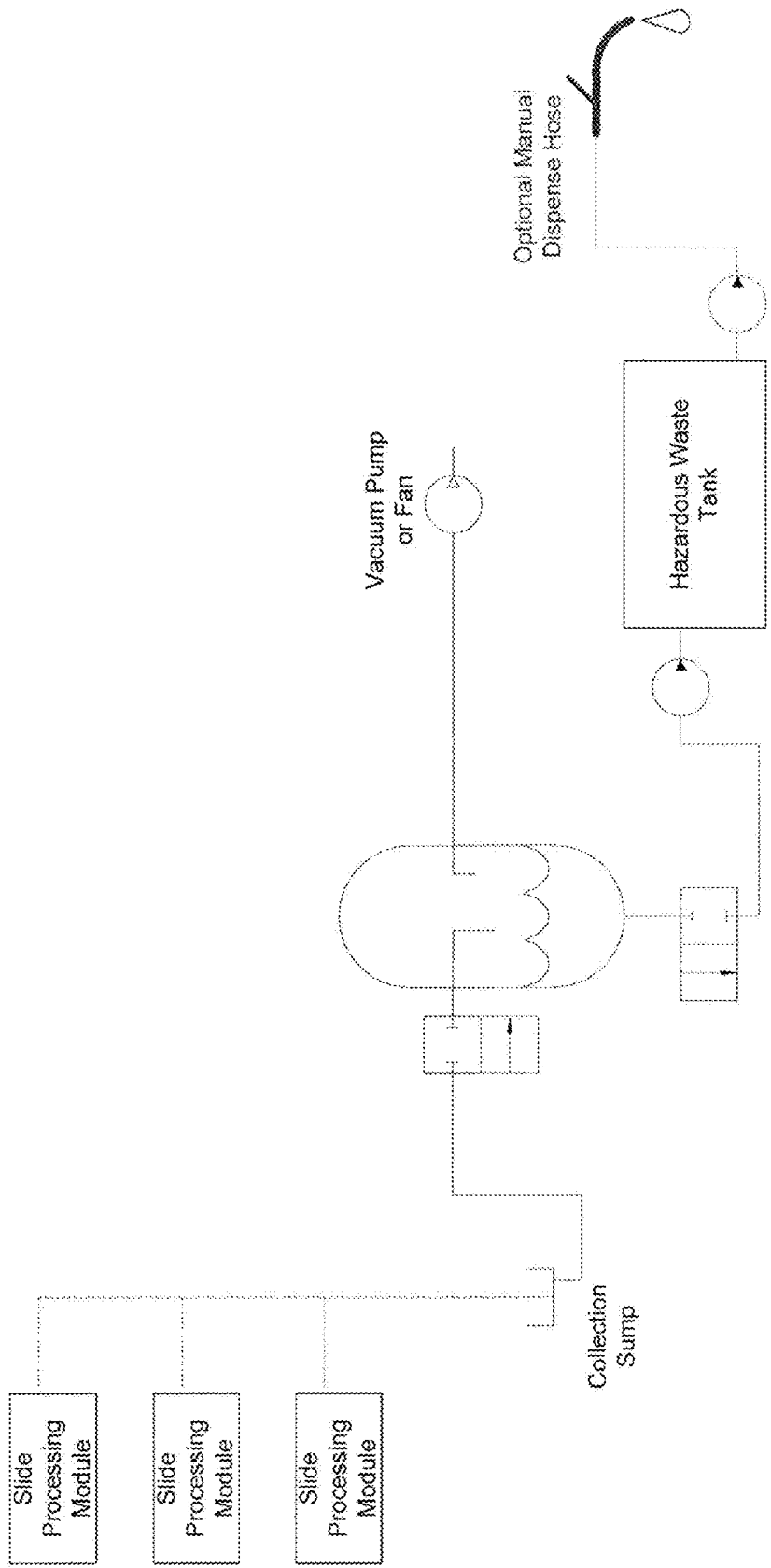
FIG. 13 is a schematic view of another waste treatment module of the system of FIG. 5.

FIGS. 11 to 13 show different configurations of a waste treatment module deployed by the apparatus 10 to treat waste arising from treating the tissue samples using one or more of the reagents. In these figures, waste from the slide treatment modules 12, shown as slide processing modules, is collected in a hazardous waste tank for processing. The waste can be forced into the tank using a vacuum pump or fan as shown in FIGS. 11 and 13, with FIG. 13 additionally having a sump. In any case, the hazardous waste tank can have a dispensing hose to dispense the waste without removing the tank from the apparatus 10. It is further envisaged that the waste treatment module treats the waste sufficiently so that the dispensing hose can be plumbed to a sink to safely dispose of the treated waste.

Figure 15:
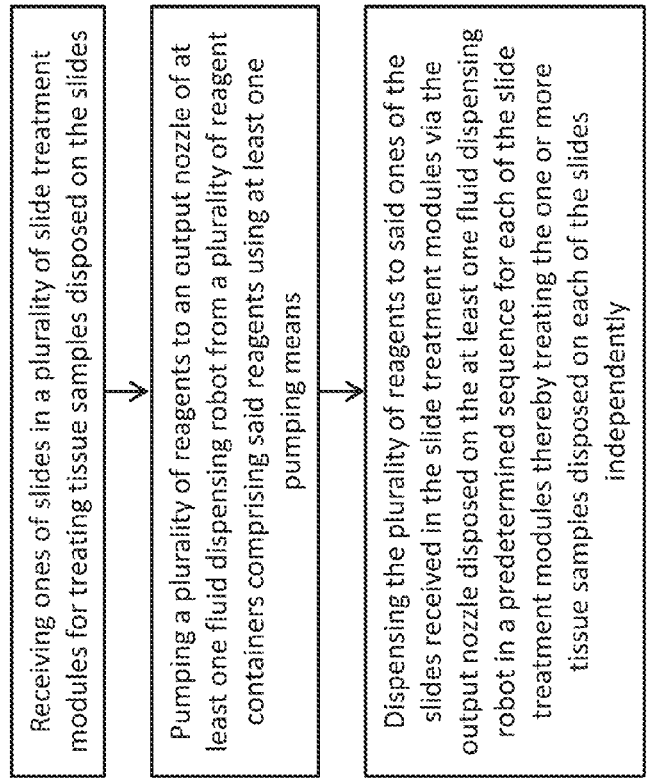
FIG. 15 is a flow chart of a method of treating one or more tissue samples according to an embodiment of the present invention.

Referring to FIG. 15, there is shown a summary of an automated method of treating one or more tissue samples disposed on slides. The method comprising the steps of receiving ones of the slides in a plurality of slide treatment modules, pumping a plurality of reagents to an output nozzle of at least one fluid dispensing robot from a plurality of reagent containers comprising said reagents using at least one pumping means, and dispensing the plurality of reagents to said ones of the slides received in the slide treatment modules via the output nozzle disposed on the at least one fluid dispensing robot in a predetermined sequence for each of the slide treatment modules thereby treating the one or more tissue samples disposed on each of the slides independently.

Further aspects of the method will be apparent from the above description of the apparatus 10. Persons skilled in the art will also appreciate that the method could be embodied in program code. The program code could be supplied in a number of ways, for example on a tangible computer readable medium, such as a disc or a memory or as a data signal or data file (for example, by transmitting it from a server).

It is to be understood that various alterations, additions and/or modifications may be made to the parts previously described without departing from the ambit of the present invention, and that, in the light of the above teachings, the present invention may be implemented in software, firmware and/or hardware in a variety of manners as would be understood by the skilled person.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

Throughout the description and claims of this specification, the word "comprise" and variations of the word, such as "comprising" and "comprises", is not intended to exclude other additives, components, integers or steps.

The invention claimed is:

1. An automated system for treating one or more tissue samples disposed on slides, the system comprising:
    a controller;
    a plurality of slide treatment modules arranged to receive ones of the slides;
    at least one fluid dispensing robot configured by the controller to dispense a plurality of reagents to said ones of the slides received in the slide treatment modules via an output nozzle disposed on the at least one fluid dispensing robot to treat said one or more tissue samples respectively; and
    at least one pumping means for pumping said reagents to the output nozzle of the at least one fluid dispensing robot from a plurality of reagent containers comprising said reagents, wherein:
    the at least one fluid dispensing robot is configured by the controller to dispense said reagents in a predetermined sequence for each of the slide treatment modules to treat the one or more tissue samples disposed on each of the slides independently,
    the at least one fluid dispensing robot comprises a fluid transfer probe (FTP) robot configured by the controller to dispense a plurality of high value reagents to said ones of the slides received in the slide treatment modules via an FTP nozzle disposed on the FTP robot to treat said one or more tissue samples respectively, and
    the FTP robot is further configured by the controller to move said slides from an input buffer module to the slide treatment modules using a transport device disposed on the FTP robot to releasably hold the slides.

2. A system as claimed in claim 1, wherein the at least one fluid dispensing robot comprises at least one bulk fluid robot (BFR) configured by the controller to dispense the plurality of reagents to said ones of the slides received in the slide treatment modules via an output nozzle disposed on the at least one BFR to treat said one or more tissue samples respectively.

3. A system as claimed in claim 2, wherein the at least one pumping means comprises a plurality of pumping means, each of said pumping means associated with each of the plurality of reagents respectively for pumping said reagents to the output nozzle of the at least one BFR from the plurality of reagent containers comprising said reagents; and
    a plurality of reagent lines associated with each of the plurality of reagents which extend from each of the reagent containers via the respective pumping means to the at least one BFR.

4. A system as claimed in claim 3, wherein the at least one BFR comprises two or more BFRs and the plurality of pumping means comprises pumping means associated with each of the plurality of reagents and with each of the BFRs.

5. A system as claimed in claim 2, wherein the at least one fluid dispensing robot comprises a fluid transfer probe (FTP) robot configured by the controller to dispense a plurality of high value reagents to said ones of the slides received in the slide treatment modules via an FTP nozzle disposed on the FTP robot to treat said one or more tissue samples respectively.

6. A system as claimed in claim 5, wherein the at least one BFR and/or the FTP robot are configured by the controller to dispense said reagents and/or said high value reagents in said predetermined sequence to stain said one or more tissue samples disposed on each of the slides independently according to a predetermined staining protocol.

7. A system as claimed in claim 6, wherein the FTP robot comprises a first syringe pumping means and a second syringe pumping means arranged to aspirate and dispense said high value reagents to/from the FTP nozzle from a plurality of high value reagent containers comprising said high value reagents according to said predetermined sequence.

8. A system as claimed in claim 7, wherein the first syringe pumping means and the second syringe pumping means are disposed in series and comprise bypass valves operable such that the first and the second syringe pumping means are arranged to aspirate and dispense said high value reagents independently.

9. A system as claimed in claim 7, wherein the first syringe pumping means and the second syringe pumping means are disposed in parallel such that the first and the second syringe pumping means are arranged to aspirate and dispense said high value reagents independently.

10. A system as claimed in claim 5, wherein the FTP robot is further configured by the controller to dispense the plurality of reagents from the plurality of reagent containers via the FTP nozzle.

11. A system as claimed in claim 5, wherein the FTP robot is further configured by the controller to perform one or both of:
   a. move said slides from an input buffer module to the slide treatment modules using a transport device disposed on the FTP robot to releasably hold the slides; and
   b. move said slides from the slide treatment modules to an output buffer module.

12. A system as claimed in claim 11, wherein the slides are disposed in one or more slide racks in the input and the output buffer modules and the FTP robot is further configured by the controller to move the slides between the slide racks in the input and the output buffer modules and the slide treatment modules.

13. A system as claimed in claim 12, wherein the FTP robot is further configured by the controller to move said slides in the slide racks between the input and the output modules and further modules for treating the one or more tissue samples disposed on the slides.

14. A system as claimed in claim 13, wherein the FTP robot is further configured by the controller to move said slide racks between the input and the output modules and the further modules using the transport device to releasably hold the slide racks.

15. A system as claimed in claim 2, further comprising sensing means for performing one or both of:
   a. sensing amount of said reagents dispensed by the at least one BFR; and
   b. sensing amount of said high value reagents dispensed by the FTP robot.

16. An automated method of treating one or more tissue samples disposed on slides, the method comprising:
   receiving ones of the slides in a plurality of slide treatment modules;
   pumping a plurality of reagents to an output nozzle of at least one fluid dispensing robot from a plurality of reagent containers comprising said reagents using at least one pumping means; and
   dispensing the plurality of reagents to said ones of the slides received in the slide treatment modules via the output nozzle disposed on the at least one fluid dispensing robot in a predetermined sequence for each of the slide treatment modules thereby treating the one or more tissue samples disposed on each of the slides independently,
   wherein the at least one fluid dispensing robot comprises a fluid transfer probe (FTP) robot configured by the controller to dispense a plurality of high value reagents to said ones of the slides received in the slide treatment modules via an FTP nozzle disposed on the FTP robot to treat said one or more tissue samples respectively, and
   wherein the FTP robot is further configured by the controller to move said slides from an input buffer module to the slide treatment modules using a transport device disposed on the FTP robot to releasably hold the slides.

17. An automated tissue sample treatment apparatus for treating one or more tissue samples disposed on slides, the apparatus comprising:
   a plurality of slide treatment modules arranged to receive ones of the slides;
   at least one fluid dispensing robot configured by the controller to dispense a plurality of reagents to said ones of the slides received in the slide treatment modules via an output nozzle disposed on the at least one fluid dispensing robot to treat said one or more tissue samples respectively; and
   at least one pumping means for pumping said reagents to the output nozzle of the at least one fluid dispensing robot from a plurality of reagent containers comprising said reagents; wherein
   the at least one fluid dispensing robot is configured by the controller to dispense said reagents in a predetermined sequence for each of the slide treatment modules to treat the one or more tissue samples disposed on each of the slides independently,
   wherein the at least one fluid dispensing robot comprises a fluid transfer probe (FTP) robot configured by the controller to dispense a plurality of high value reagents to said ones of the slides received in the slide treatment modules via an FTP nozzle disposed on the FTP robot to treat said one or more tissue samples respectively, and
   wherein the FTP robot is further configured by the controller to move said slides from an input buffer module to the slide treatment modules using a transport device disposed on the FTP robot to releasably hold the slides.

* * * * *